(12) United States Patent
Huang et al.

(10) Patent No.: US 7,632,016 B1
(45) Date of Patent: Dec. 15, 2009

(54) DIGITAL DETECTOR CALIBRATION WITH KNOWN EXPOSURE

(75) Inventors: Weidong Huang, Fairport, NY (US); Chang-Ying Joseph Yang, Webster, NY (US)

(73) Assignee: Carestream Health, Inc., Rochester, NY (US)

( * ) Notice: Subject to any disclaimer, the term of this patent is extended or adjusted under 35 U.S.C. 154(b) by 0 days.

(21) Appl. No.: 12/177,172

(22) Filed: Jul. 22, 2008

(51) Int. Cl.
*G01D 18/00* (2006.01)
(52) U.S. Cl. ...................................... 378/207
(58) Field of Classification Search ................. 378/204, 378/207; 250/252.1, 363.09
See application file for complete search history.

(56) References Cited

U.S. PATENT DOCUMENTS

| | | | |
|---|---|---|---|
| 5,617,462 A | 4/1997 | Spratt | |
| 6,192,105 B1 | 2/2001 | Hunter et al. | |
| 6,944,266 B2 | 9/2005 | Yamazaki et al. | |

*Primary Examiner*—Jurie Yun

(57) ABSTRACT

A method for calibrating a digital X-ray detector executed at least in part by a control logic processor. A radiation sensor is disposed along the optical path that extends between a radiation emitter and the digital X-ray detector. A set of radiation beam conditions for X-ray generation is selected and digital image values from the digital X-ray detector are obtained in one or more iterations of providing a threshold signal to radiation control logic, the threshold signal corresponding to a predetermined exposure level, exposing both the digital X-ray detector and the radiation sensor to radiation and terminating the exposure according to a comparison of the threshold signal with a signal from the radiation sensor that indicates an accumulated radiation level, then obtaining the digital image values from the digital X-ray detector. One or more sets of calibration values are generated according to the obtained digital image values.

20 Claims, 6 Drawing Sheets

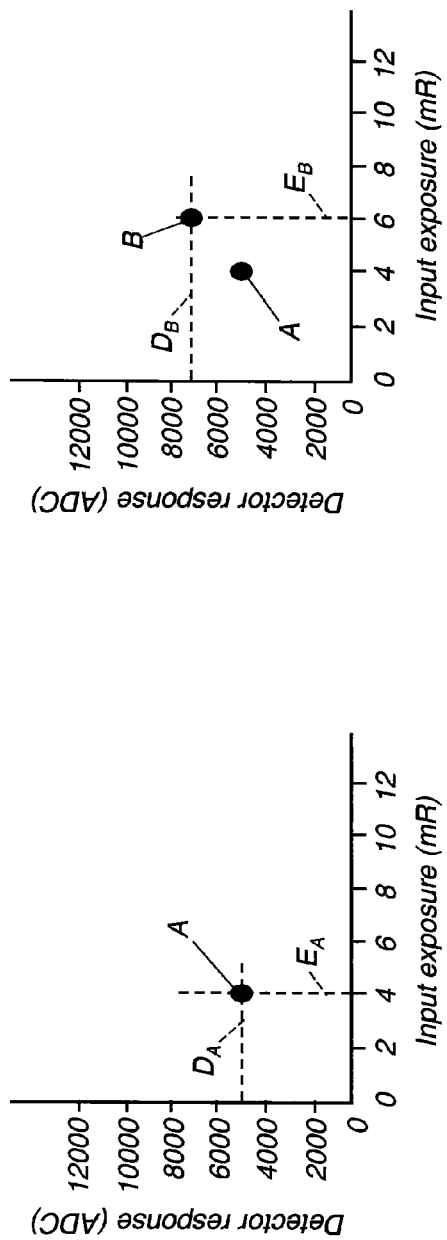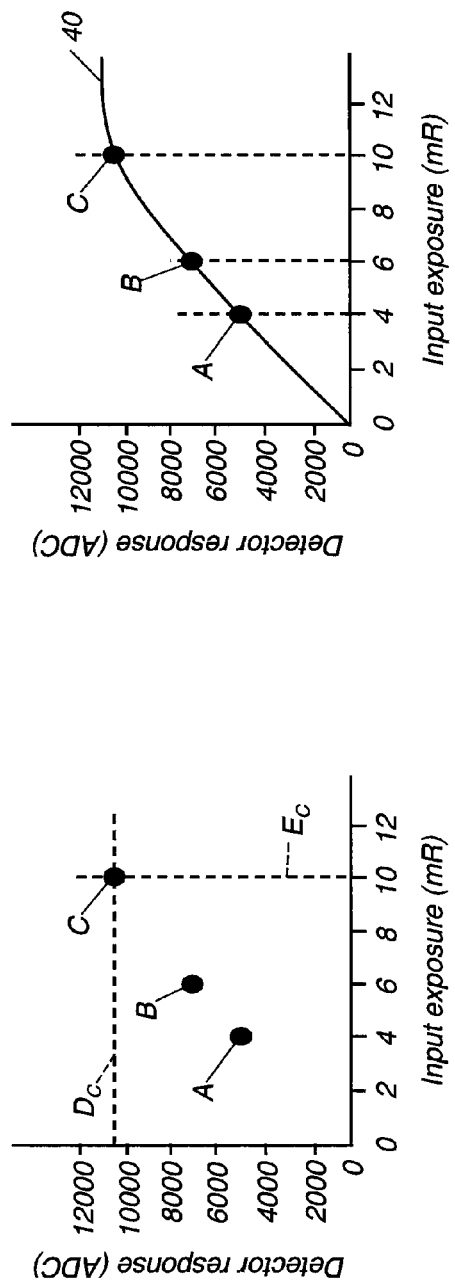

DIGITAL DETECTOR CALIBRATION WITH KNOWN EXPOSURE

FIELD OF THE INVENTION

This invention generally relates to X-ray imaging and more particularly relates to a method for providing a predetermined exposure level for calibration of a digital radiology (DR) detector using an Automatic Exposure Control (AEC) device.

BACKGROUND OF THE INVENTION

Digital Radiography (DR) systems offer benefits and advantages over film-based systems and are used increasingly for diagnostic imaging in numerous applications. Unlike its earlier film predecessor, the DR detector panel forms an image by collecting electronic signals from thousands of pixels in its detector array, each signal level indicative of the amount of X-ray radiation that is detected. While this arrangement can serve as a capable alternative to the conventional film cassette and offers a number of capabilities for improved image processing and display, however, there can be considerable complexity involved in calibrating the DR panel so that it delivers a uniform and well-characterized response over the full range of radiation levels received.

A related area of difficulty that is familiar to those skilled in the diagnostic imaging arts relates to differences in response to exposure from one imaging system to the next, particularly between the response of earlier film-based systems and the response of systems using DR digital sensors. In general, film response follows the familiar D-log E sigmoid-shaped curve and allows a more limited range than does digital response. Digital sensors offer a wider dynamic range for clinical imaging, in part, because their output data can be readily manipulated to compensate for response characteristics. Differences such as these between digital and film detection characteristics for X-ray exposure have been noted and addressed in the art using various techniques, adapted for obtaining clinically useful images.

The response of the DR detector is calibrated before a system can be used to acquire clinical images. This detector calibration serves a number of purposes, including: (i) compensating for differences among individual sensors that relate to sensitivity and to dark signal response; (ii) compensating for differences in gain and offset response among individual signal channels of the amplification and digitization electronics; (iii) compensating for non-uniformity of the X-ray field; (iv) establishing a known (or relative) arithmetic relationship (for example, linear or logarithmic) between detector response (for example, analog-digital converter or ADC counts) and incident radiation dosage at the detector surface; and (v) additional processing, for example, identifying defective pixels, could also be part of the detector calibration task.

As described earlier, the response of digital devices is generally linear, at least to an approximation of the first order. Thus, in conventional practice, DR systems typically use a simple linear correction to calibrate for detector response. However, it is known that linear extrapolation may be inaccurate over portions of the exposure range. The graph of FIG. 1 shows exemplary detector response to exposure for various DR detectors. A dotted line 42 indicates ideal linear response for a DR detector. The actual response of a detection component is more accurately shown, in this example, by a solid curve 40. As can be seen from this graph, the response of the DR detector is substantially linear for input exposures of up to about 6 mR in this example. As exposure levels increase above this level, however, a simple linear calibration becomes progressively less accurate. If a linear approximation were used where there is such a response, image artifacts would appear over higher exposure regions after the linear correction is applied. For many types of images, this could result in banding, with strips appearing near a skin line for a conventional chest X-ray image. Non-linear response for higher exposure values applies, for example, for the Trixell Pixium 4600 detector from Trixell Inc., Morains, FR, and other similar devices.

It is noted that the problem exhibited in FIG. 1 can be more or less noticeable at different kVp levels. Thus, for example, the same DR detector may exhibit different response characteristic and a different amount of non-linearity depending on the particular exposure kVp settings that are used.

If the response of a DR detector were truly linear, it would only be necessary to measure response at two different arbitrary exposure levels, including zero exposure level (i.e. dark) where no radiation is given. Because any two points along the line are sufficient to define the line, this would provide sufficient offset and gain information for linear calibration. However, where linear response does not apply, as shown in the upper range of the example of FIG. 1, the response of the detector needs to be measured at more than two exposure points in order to characterize its response behavior more accurately. This would enable its response to be more suitably characterized with a higher order polynomial formula or other appropriate non-linear mathematical approximation function. Moreover, for non-linear mapping, it now becomes relevant to identify, as closely as possible, the input exposure levels (or, at least, relative relationship between the exposure levels) at which the detector responses are to be measured. Doing this allows proper correction to be applied for a raw image with improved accuracy, resulting in eliminating or at least diminishing image artifacts such as banding.

Conventionally, determining the exposure levels used in DR detector calibration requires use of dosimetric instruments and involves tedious routines with repetitive setup, exposure, and reading and processing operations. For example, once the X-ray exposure technique is chosen, the actual exposure reaching the detector is typically measured with a dose meter placed in front of the detector. Additional measurements are required if more exposure levels are used. The exposure information that is obtained is not only subject to error due to accuracies of the dosimetric instrument and the experimental setup, but also depends on the stability of the radiation output of the X-ray generator unit. In addition, when a detector calibration needs to be repeated at a later time, the exposure levels measured from previous calibration setup would need to be re-measured. This is because any variations in the experimental setup, including geometry differences and X-ray generator output variation, for example, can change the radiation exposure reaching the detectors and thus compromise the accuracy of the calibration result.

Clearly, performing thorough DR detector calibration involving multiple exposure levels can become a tedious and labor-intensive process. As a result, compromises such as linear approximation and interpolation are often made in practice, in order to save cost and labor, to minimize error, and to minimize overall calibration downtime.

With the growing importance of DR diagnostic imaging and the drive to improve diagnostic tools and the efficiency of medical care in general, there is, then, a need for improved methods for DR detector calibration that can be performed at reduced cost, that allows a high degree of accuracy, and that offer the capability for automation without extensive operator activity or interaction.

SUMMARY OF THE INVENTION

It is an object of the present invention to provide a method of delivering X-ray radiation of pre-determined exposures suitable for the purpose of calibration of the digital detectors in an X-ray imaging apparatus. With this object in mind, the present invention provides a method for calibrating a digital X-ray detector executed at least in part by a control logic processor and comprising: a) disposing a radiation sensor along the optical path that extends between a radiation emitter and the digital X-ray detector; b) selecting a set of radiation beam conditions for X-ray generation; c) obtaining digital image values from the digital X-ray detector in one or more iterations of: (i) providing a threshold signal to radiation control logic, the threshold signal corresponding to a predetermined exposure level; (ii) exposing both the digital X-ray detector and the radiation sensor to radiation, and terminating the exposure according to a comparison of the threshold signal with a signal from the radiation sensor that indicates an accumulated radiation level; (iii) obtaining the digital image values from the digital X-ray detector; and d) generating one or more sets of calibration values according to the obtained digital image values.

It is a feature of the present invention that it uses the AEC control loop to set up a variable exposure level according to a variable reference threshold.

It is an advantage of the present invention that it allows an X-ray imaging apparatus to deliver a known exposure at a given kVp level.

It is a further advantage of the present invention that it allows successive exposures to be delivered to the detector with improved accuracy that is less sensitive to conditions such as variations in geometry arrangement of the equipment and in the radiation output of the X-ray generator unit.

It is a further advantage of the present invention that it adapts conventional AEC apparatus for the purpose of controlling exposure levels over the broader range afforded by a digital detector.

These and other objects, features, and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

While the specification concludes with claims particularly pointing out and distinctly claiming the subject matter of the present invention, it is believed that the invention will be better understood from the following description when taken in conjunction with the accompanying drawings.

FIGS. 6A through 6D show how individual measurements are used to form a calibration response curve.

DETAILED DESCRIPTION OF THE INVENTION

The present description is directed in particular to elements forming part of, or cooperating more directly with, apparatus in accordance with the invention. It is to be understood that elements not specifically shown or described may take various forms well known to those skilled in the art.

In the context of the present disclosure, the term "radiation beam conditions" relates to the parameters used for generation of the X-ray radiation and forms a set of conditions that includes at least one or more of the following parameters:

(i) A kVp value indicative of beam energy;

(ii) An mA value indicative of beam intensity;

(iii) One or more X-ray filter materials;

(iv) A source-to-image distance (SID) between the radiation emitter and the digital X-ray detector.

Embodiments of the present invention address the problem of DR detector calibration by employing a radiation sensor, such as that provided by Automatic Exposure Control (AEC) components of the DR system. Conventionally used for terminating X-ray emission according to predetermined exposure levels during patient imaging, the AEC apparatus of the conventional X-ray system serves embodiments of the present invention by acting as its sensing instrumentation for exposure over a range of values. By expanding upon the original and normal function of the AEC, the method and apparatus of these embodiments of the present invention allow DR detector calibration to be readily performed at regular intervals, including the option of automated calibration processing for improved performance and efficiency of the DR system.

For a better understanding of the present invention, it is useful to first consider the basic components of the DR imaging system and the conventional role of the AEC in such a system. Automatic Exposure Control (AEC) apparatus are widely used in conventional diagnostic X-ray equipment to control X-ray exposure levels received by a patient. Using an AEC device, a radiology technician can help to limit the amount of radiation that is received by sensing the radiation level and providing an output signal that indicates when sufficient radiation has been received. This output signal is then used to disable power to the X-ray emission components, thereby stopping the generation of ionizing radiation.

Figure 1:
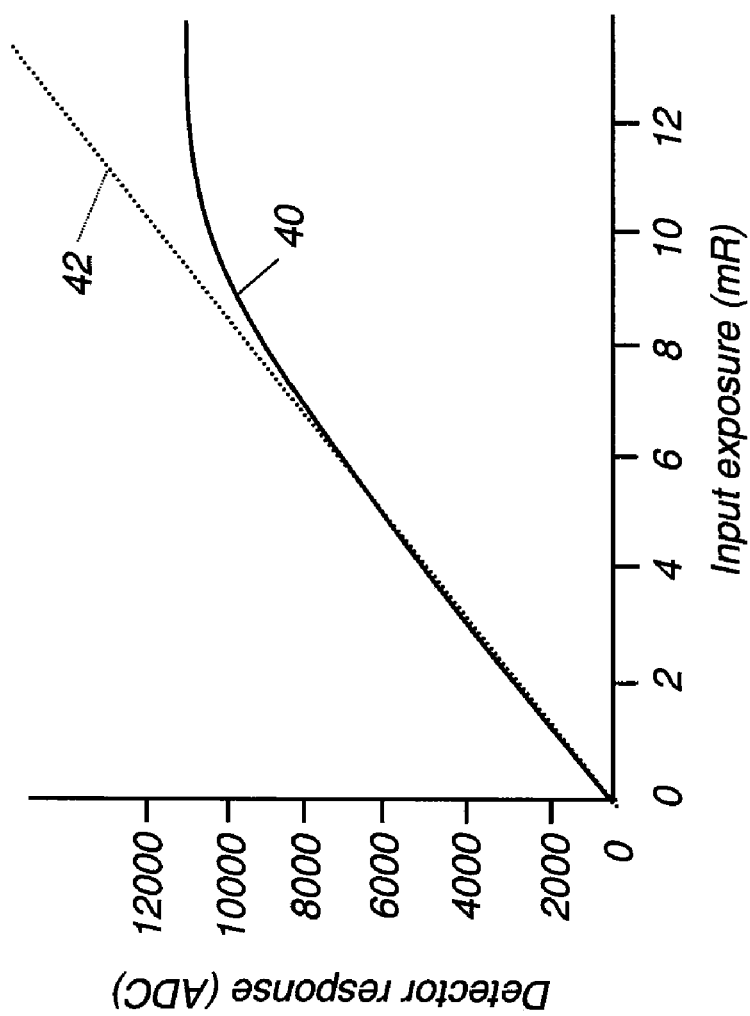
FIG. 1 is a graph showing a non-linear response characteristic of a digital detector.
Figure 2:
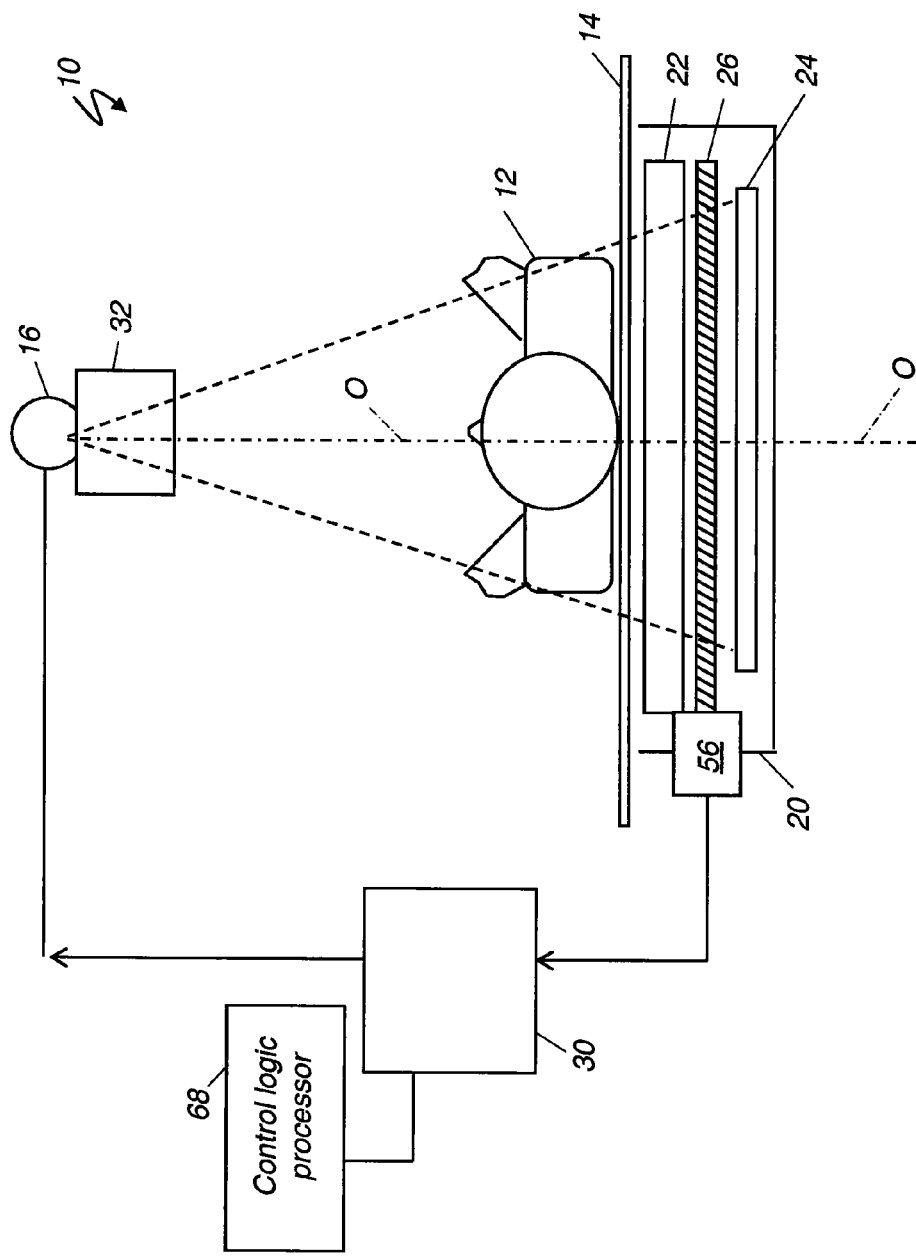
FIG. 2 is a schematic block diagram showing an X-ray apparatus for digital imaging.

Referring to FIG. 2, there is shown a schematic of an X-ray apparatus 10 used to provide an X-ray image from a patient 12. Patient 12 is placed against a support, such as a table top 14 that is situated a suitable distance from an X-ray emitter 16. Behind patient 12, typically fitted into a bucky 20 (Potter-Bucky apparatus) are a grid 22, a detector 24, and an AEC sensor 26 that has an associated gain circuit 56, described in more detail subsequently. AEC sensor 26 or other suitable radiation sensor may be positioned at any suitable point along the optical path O that extends between, and possibly beyond, X-ray emitter 16 and digital X-ray detector 24. For example, a sensor may even be embedded as part of the detector. In the embodiment of FIG. 2, X-rays that pass through patient 12 are directed through grid 22 to reduce scattering effects and, after transmission through AEC sensor 26, are incident on detector 24 that obtains the image. AEC sensor 26, substantially transparent to the radiation, monitors the level of incident X-rays and provides a corresponding output signal to an X-ray controller 30, circuitry that is a part of the X-ray generator that controls the operation of emitter 16. A collimator 32 is typically used for providing a suitable aperture for each imaging situation.

Originally, the AEC control loop that includes AEC sensor 26, gain circuit 56, controller 30, and emitter 16 was devised for use with film-based systems. With these earlier systems, the purpose of the AEC control loop was to provide a consistent density for film images, based on variables such film speed and equipment kVp setting. Using the AEC with a film-based system, it becomes possible to limit the radiation emission to just the amount needed in order to obtain a certain image density on the film. More recently, the AEC device has shown itself to be adaptable, for the same functions, to digital radiographic systems. That is, with reference to the system of FIG. 2, detector 24 may be a film cassette, a Computed Radiography (CR) cassette, or a Digital Radiography (DR) detector array. With digital imaging apparatus, the AEC sensor performs the same primary function, limiting the appropriate radiation doses to the patient for obtaining clinically useful images.

A control logic processor 68, shown outside X-ray controller 30 in the exemplary embodiment of FIG. 2, executes control logic instructions for handling and responding to AEC signals. In embodiments of the present invention, control logic instructions accessed by or stored within control logic processor 68 perform the needed functions for at least partial automation of calibration processing. Control logic processor 68 may be any type of logic processing device, including a computer, dedicated processor, application-specific integrated circuit (ASIC), or microprocessor or other device.

How the AEC Operates

AEC sensor 26 typically uses one or more ionization chambers or solid-state detectors that are interposed in the path of the radiation, along the optical path that extends between the radiation emitter and digital X-ray detector, in front of or behind the X-ray detector with respect to the radiation, as was shown in FIG. 2. The signal output of these devices, integrated over time, helps to measure the amount of radiation received. The AEC control loop is designed to sense a threshold signal level that corresponds to a given exposure level and to terminate X-ray generation at this threshold. In practice, different signal thresholds apply for different kVp settings and other radiation beam conditions, providing a suitable cutoff dose for each kVp level that can be used for X-ray emitter 16. Conventionally, the AEC control loop uses one or more compensation curves, sets of reference threshold values that indicate suitable exposure levels at different radiation beam conditions. For example, U.S. Pat. No. 4,454,606, entitled "Reconfigurable X-Ray AEC Compensation" to Relihan describes memory circuitry associated with the AEC for storage of this type of reference threshold value.

The AEC device itself is calibrated to respond to the necessary exposure level needed for an imaging application under different radiation beam conditions. For example, U.S. Pat. No. 6,192,105 entitled "Method and Device to Calibrate an Automatic Exposure Control Device in an X-ray Imaging System" to Hunter et al. describes the calibration of the AEC sensor itself for achieving pre-determined exposure levels that are suitable for use with a digital detector for acquiring patient images. Similarly, U.S. Pat. No. 5,617,462 entitled "Automatic X-Ray Exposure Control System and Method of Use" to Spratt describes storage of multiple tables of predetermined exposure data values for the AEC, with different tables to support different characteristic anatomy types. U.S. Pat. No. 6,944,266 entitled "X-Ray Imaging Apparatus" to Yamazaki et al. describes AEC pixel calibration where the AEC device itself is pixel-based and where AEC pixel components themselves can have different response characteristics. Calibration of the AEC itself, as conventionally practiced, is a prerequisite for using the methods and apparatus of the present invention.

Figure 3:
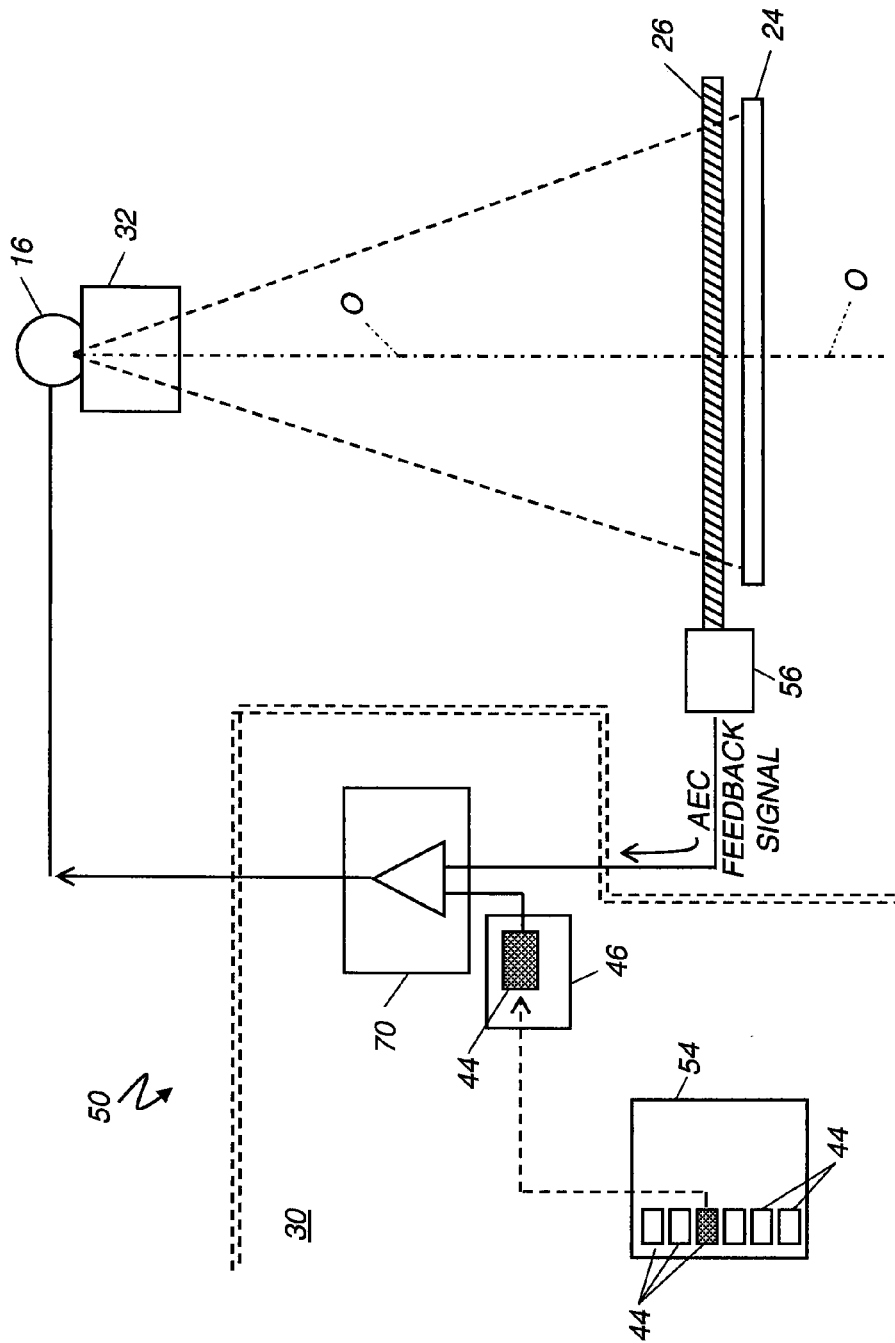
FIG. 3 is a schematic block diagram showing a conventional AEC control loop.

As noted earlier, embodiments of the present invention extend AEC utility to a new purpose, adapting its performance and behavior so that, in addition to its designed function of responding to incident radiation for deactivating emitter 16 at a predetermined threshold level, it also serves as a radiation sensor usable for DR detector 24 calibration. The block diagram of FIG. 3 shows a simplified schematic of an AEC control loop 50 as conventionally used for patient exposure. It is useful to have an overview of this control and feedback loop, since this same control loop is adapted to serve the task of detector calibration 26 using the methods of the present invention.

Within controller 30, a table 54 stores reference threshold values that control the exposure that is generated from X-ray emitter 16. Table 54 typically holds multiple threshold values 44, each value 44 associated with a set of radiation beam conditions, or setup parameters, that are used together for generating a specific type of image. For example, one value may be used for exposure at 80 kVp; another value is used for exposure at 110 kVp. There is, then, an associated value 44 associated with each of these setup kVp and related radiation beam condition settings. When a patient image is to be obtained, the corresponding value 44 is loaded as a digital signal into a register 46. This loaded value 44 is then used by controller 30 in order to set the threshold level for turning emitter 16 off. The resulting signal level is then compared against the AEC feedback signal from gain circuit 56 on the AEC by a comparator 70, or other similar circuit. The result of this comparison function is then used to disable emitter 16 when the appropriate exposure has been obtained.

It is instructive to note that comparator 70 as shown in controller 30 is illustrative and can be embodied in a number of different ways, including loading value 44 into register 46 as just described. Alternately, some other type of signal can be provided to comparator 70, or to a similar process or circuitry, for comparison against the AEC feedback signal from gain circuit 56. For example, the AEC signal may be an analog signal. In this case, control logic can provide an analog signal, rather than a digital signal, that indicates a threshold level for comparison with the AEC feedback signal.

Most modern designs of the AEC control logic that are conventionally implemented in X-ray generator systems provide some way to allow dynamic and repeatable modification of the threshold values (from table 54 in FIG. 3) or, alternately, the threshold signal used for comparison with the AEC feedback signal. For example, the AEC system implemented on a CPI generator (CPI International, Palo Alto, Calif.) maintains an internal 7 entry table, sometimes called the AEC compensation table, with each entry in the table storing the reference threshold value to be used for one of the following kVp radiation beam conditions: 55, 65, 75, 85, 95, 110, and 130 kVp, respectively. When one of the above kVp beam conditions is selected, the corresponding threshold value 44 in table 54 is loaded as the value 44 entry in register 46, in order to obtain the desired AEC cutoff dose for the selected kVp beam. For X-ray beams having other radiation beam conditions, a linear interpolation may be used automatically by the generator controller 30 firmware based on the two nearest reference values from table 54 to obtain the new reference threshold value. Conventionally, the AEC compensation values stored in table 54 are settings from the manufacturer that provide exposure levels suitable for acquiring clinical images.

Still referring to FIG. 3, the signal from AEC sensor 26 goes to gain circuit 56. When the output signal from gain circuit 56 exceeds the reference threshold set by the selected value 44 in register 46, the output signal of controller 30 turns X-ray emitter 16 off.

Figure 4:
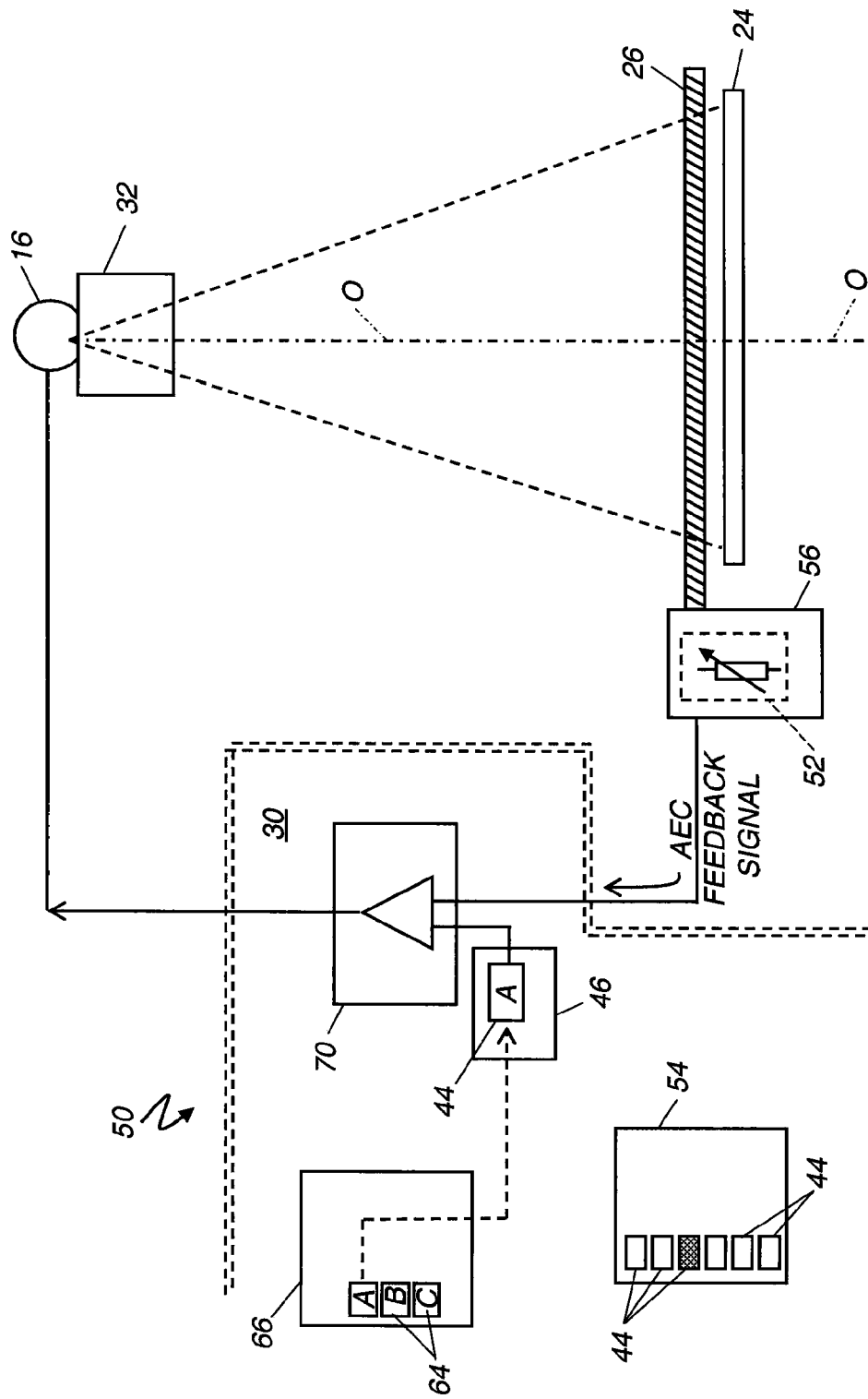
FIG. 4 is a schematic block diagram showing a modified AEC control loop according to the present invention.

FIG. 4 then shows how control loop 50 is modified in order to use AEC sensor 26 to calibrate detector 24 in one embodiment. Of particular interest are two modifications:

(i) Adjustment to gain circuit 56, shown as gain control 52; and (ii) Set of one or more calibration tables 66 with alternate values 64.

Gain adjustment (i) may be needed when the particular AEC control loop that is used at the site is limited to a range that varies from the range needed for detector 24 calibration. Methods for range control and more detailed information on how this is accomplished in various embodiments are given subsequently.

The use of one or more alternate calibration tables 66 ((ii) above) enables control loop 50 to operate at the particular values that are needed in order to calibrate detector 24 at two or more points, according to its characteristic response curve. Exemplary values A, B, and C in FIG. 4 are used in subsequent description as exposure values for measurement and generation of a characteristic response curve that is then used for DR detector 24 calibration. In practice, other storage data structures could be used to provide the alternate values needed for calibration; for clarity of description, the basic model shown in FIG. 4 is described. The specific threshold values A, B, and C shown in the example of FIG. 4 depend on characteristics of the DR detector device that is to be calibrated, as is described subsequently.

The basic sequence for using AEC control loop 50 to calibrate detector 24 is as follows:

a) condition the AEC feedback signal for the range of exposure values needed;

b) repeat the following sequence for each of the one or more points needed for detector calibration:

1) Load a calibration value (for A, B, or C in FIG. 4) or other signal in controller 30 for specifying an exposure threshold;

2) Run an exposure, terminating exposure when the specified exposure threshold is met;

3) Obtain the resulting digital value for that exposure from detector 24.

The sequence given in step b) may be repeated for calibration at one or more exposure threshold values. The sequence given in a) and b) can be repeated for calibration at one set of radiation beam conditions, such as to obtain data that can be statistically processed to provide more robust calibration results. Alternately, more than one set of radiation beam conditions is used in successive iterations, such as at additional kVp power levels. These steps could be carried out manually, requiring the operator to follow a sequence of procedures that obtain each in a series of measured values in sequence. However, it can be readily observed that automated or partially automated methods for calibration offer many advantages, including more efficient use of operator time and elimination of data entry or command entry error. Subsequent processing can then use the obtained data in order to generate one or more sets of calibration values for use with digital image data values.

Figure 5:
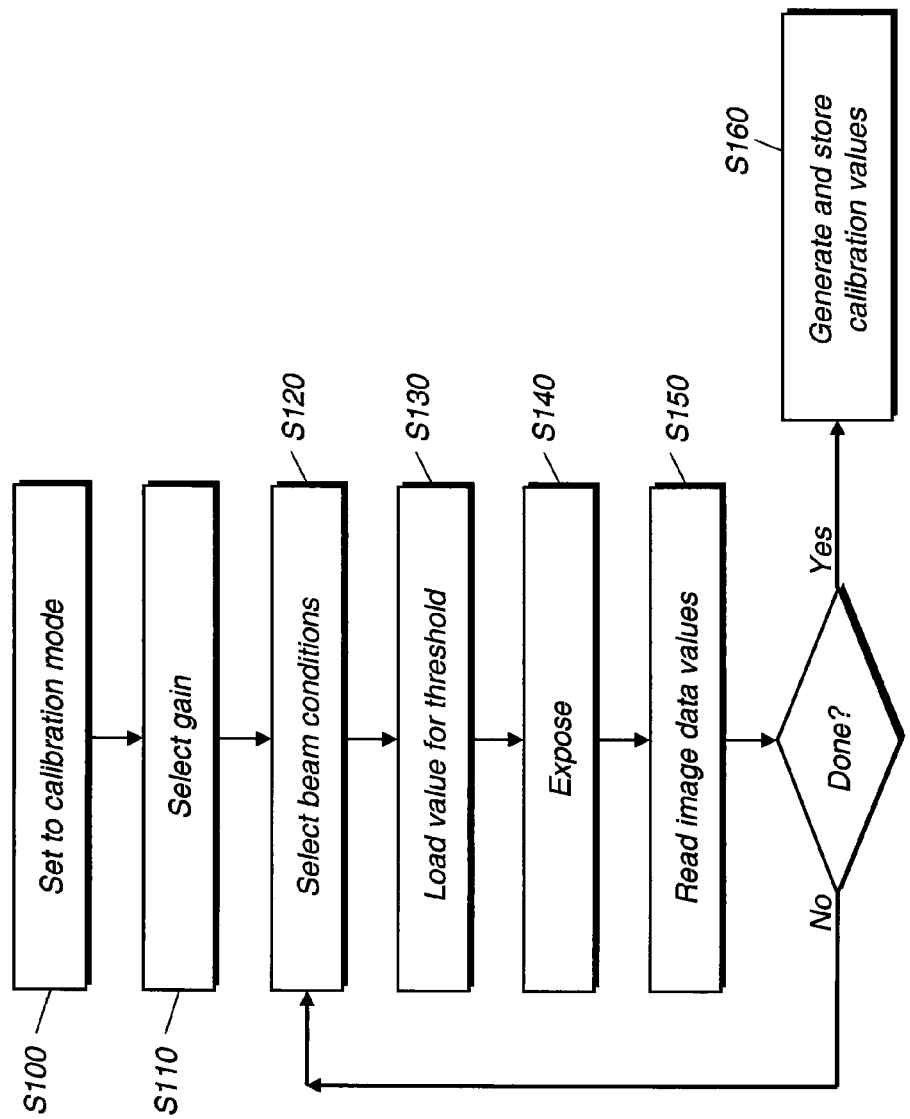
FIG. 5 is a logic flow diagram that shows the basic sequence used in an automated embodiment.

The flow diagram of FIG. 5 shows a sequence for automated calibration according to one embodiment. In an initialization step S100, the operator/technician provides a command to select calibration mode instead of normal patient imaging mode. A gain selection step S110 then sets the gain of AEC control loop 50 to a suitable level for DR detector calibration. A repeated sequence then follows, first setting radiation beam conditions in a beam conditions selection step S120. A load value step S130 then loads an appropriate calibration value 64 (FIG. 4) as a digital signal to the control circuitry for the AEC loop. This is one method of providing a reference threshold signal; an alternate embodiment provides an analog signal that corresponds to the reference threshold value. Exposure takes place in a step S140, followed by reading and storage of the data in a reading step S150.

In practice, exposure initiation itself may require technician response, such as by pressing an exposure control when prompted, for example. Steps S120-S150 repeat until all of the needed exposures have been provided and their corresponding data values have been read. Once all data has been collected, a correction values generation step S160 is carried out, forming the LUT, formula, or other data structure that stores one or more sets of required calibration compensation parameters that serve as calibration values. Beam conditions selection step S120 may specify the same or different beam conditions upon subsequent iterations.

For each of one or more sets of beam conditions, one or more calibration values 64, shown as A, B, C in the schematic block diagram of FIG. 4, are chosen for the specific DR detector 24 and AEC panel 26 used in an application. The number of calibration values that are needed depends on the response characteristics of the DR panel and on how closely this response needs to be calibrated.

By way of example, the progression shown in FIGS. 6A-6C show, using three calibration values A, B, and C, how the characteristic calibration response curve in FIG. 6D is generated using the sequence just given. Each value A, B, and C is successively loaded to register 46 as a threshold value using the arrangement described earlier with reference to FIGS. 3 and 4. FIG. 6A shows a first point on the calibration curve established using value A. FIG. 6B shows a second point on the calibration curve established using value B. FIG. 6C shows a third point on the calibration curve established using value C. FIG. 6D then shows the resulting curve 40 that is generated using the measurements obtained from using values A, B, and C.

It can be appreciated from the example given in FIGS. 6A-6D that calibration curve 40 can be generated using any number of suitable points. Where a detector has a highly linear response over the exposure range of interest, only one or two points are necessary. One point allows a linear relationship to be obtained where the reference point uses a dark reading or simply approximates using the origin (0, 0), with appropriate offset compensation for "dark image" noise. Where response varies from linearity, three or more measurement points are generally obtained. Calculations and algorithms usable for generating more complex calibration curves, such as with polynomial curve-fitting, are well known to those skilled in the art of imaging detector calibration.

The detector array typically contains well over 1,000,000 pixels. The task of calibration is to adjust for measurement differences between pixels that receive the same exposure. Curve 40 shown in FIG. 6D thus represents a target curve to which values for individual pixels are adjusted as a result of calibration. It can be readily understood that improved calibration accuracy is provided where multiple measurements are obtained. In one example embodiment, doses nominally at 15%, 30%, 45%, 60%, and 90% of a 50 µGy range with beam conditions at 85 kVp are used. With a linear proportion of threshold value to AEC cutoff dose, and a full range value of 10, the corresponding threshold values at 85 kVp would be 1.5, 3, 4.5, 6, 7.5, and 9 respectively. This same sequence can then be repeated for other beam conditions, as needed. The resulting images can then be assessed to calculate correction parameters for calibration of each pixel in the detector, using calibration logic familiar to those skilled in the image processing arts.

It is instructive to point out that different AEC systems have different ranges of achievable exposures and may utilize different methods for storing and using reference threshold data. The approach described herein with reference to AEC control loop 50 embodiments such as that shown in FIG. 4 can be adapted to other AEC embodiments, making the method and apparatus of the present invention usable with any of a number of existing digital radiography systems.

How Calibration Values are Determined

One or more calibration values, shown as values A, B, and C in the examples of FIGS. 4 and 6A-6D are used for calibration of the DR detector at a given set of beam conditions. In order to determine the number of calibration values needed and their corresponding exposure settings ($E_A$, $E_B$, and $E_C$, respectively), it is helpful to have information from the supplier or manufacturer of the DR detector. For example, some DR detectors may exhibit a substantially linear response characteristic, thus indicating that selection of just one or two calibration values would be appropriate. With increased divergence from linearity, the use of additional calibration values would be desirable.

As shown in the example of FIGS. 6A-6D, each calibration value A, B, C maps an exposure value ($E_A$, $E_B$, and $E_C$, respectively) to a corresponding digital value ($D_A$, $D_B$, and $D_C$, respectively) received from the detector ADC for that exposure. Thus, an initial step in setting up calibration is to identify an appropriate set of exposure values, for example, a set of three values $\{E_A, E_B, E_C\}$, as required by the calibration algorithm, and the corresponding threshold values $\{a, b, c\}$. Then, for each exposure value in the set $\{E_A, E_B, E_C\}$, one or more dosimeter measurements can be used, based on trial-and-error measurement or on previously obtained data. (For example, the relationship between the threshold value a and its corresponding exposure $E_A$ reaching the detector may be measured in advance or provided by the manufacturer.) Then, it is necessary to ascertain how to determine the threshold value in order to achieve the given exposure value at the precision needed. For doing this, the existing AEC utilities can be used to correlate AEC shutoff response with a measured exposure value. This can be an iterative process, with fine-tuning adjustments made to AEC control circuitry and threshold signals until the desired exposure level is obtained for each of the set of exposure values $\{E_A, E_B, E_C\}$. The set of exposure values $\{E_A, E_B, E_C\}$ and their corresponding threshold values $\{a, b, c\}$ are then stored for use in the calibration process.

Once AEC response characteristics are known for obtaining different exposure levels (such as those shown at points A, B, and C in the example of FIGS. 6A-6D just described), this process for determining calibration values can be easily repeated for one or more additional sets of beam conditions.

Gain Adjustment

As described earlier with reference to FIG. 4, it may be necessary to provide gain adjustment over conventional AEC equipment in order to properly condition control loop 50 so that it allows the appropriate response range for digital detector calibration. Adjustment to broaden the response range is generally needed because AEC apparatus were originally designed for use with a screened film-based radiography system that typically has a narrower exposure range than that provided by DR detectors.

As an example, when used with 400-speed class chest X-ray films, the AEC is typically operated to achieve approximately ~4 µGy cutoff dose. With 400 speed film, this cutoff dosage corresponds to ~1.6 optical density in the region of interest, assuming the γ value of the film is ~3. Additional density controls on the X-ray generator console may increase or decrease the doses by a nominal factor. For example, most generator consoles typically provide "+" or "−" settings of adjustment in the form of density controls. Each "+" or "−" change in density setting will cause, for example, 25% change in dose. For a 200-speed class film, the AEC cutoff dose is likely about ~8 µGy, doubling the dose of a 400-speed setting. Overall, approximately 16 µGy is a typical upper limit for AEC-controlled exposure with much of the currently installed base of DR systems.

In general, the dosage range of film is much more limited than that of digital detectors. In order to use AEC functions to generate a series of exposures with doses that may be required to cover the range of the detector response, for example, with a Kodak Pixium 4600 detector used in DR7500/9000 system, the dose range of interest would range up to about ~80 µGy under the conventional RQA-5 beam. As can be readily seen, this dose range is an order of magnitude larger than the film-based dose level for which the AEC is conventionally used. AEC circuitry designed for this conventional film-based system may not have sufficient range for the response range required for the digital detector calibration.

Referring back to FIG. 4, gain control 52 is used to adapt the range of the AEC suitably for digital detector calibration. There can be a number of ways by which gain control 52 is added for conditioning the gain in AEC feedback loop 50. Exemplary embodiments of the present invention use methods for gain control that can include the following:

(i) Modification to existing AEC circuitry. This approach can include modifying the AEC hardware itself, such as adding additional components to allow adjustment to gain circuit 56 or changing firmware, or software at controller 30.

(ii) Adding external hardware for conditioning the AEC feedback signal. Depending on the hardware configuration, addition of an interface unit for AEC signal conditioning may be most advantageous. Relative to FIG. 4, this would entail conditioning the AEC feedback signal in some way, along its path between gain circuit 56 and controller 30.

(iii) Modifying the response of generator control logic for X-ray emitter 16. Where feasible, modifications to controlling circuitry or software can be used to adapt the response of the control logic that monitors and controls the X-ray generator itself.

Observe that any of the changes given above in (i)-(iii) are done without interfering with conventional functioning of the AEC used for patient imaging. Hardware may be toggled or otherwise switched to a special calibration mode, for example, using the different gain setting or settings that this requires until calibration is complete.

In one embodiment of the present invention, an operator interface is provided for prompting an operator for entry of certain parameters or other values, such as entry or selection of a set of radiation beam conditions, for example. The operator interface also includes a control command entry interface, such as a pushbutton or other mechanism, for initiating each exposure. In an alternate embodiment, fully automated processing is provided, performing detector calibration at set periodic intervals or upon command entry by the operator.

The calibration values that are obtained using the method of the present invention can be combined with digital image values that are obtained from an image of the patient. For example, the calibration values can be subtracted from the actual image values.

The apparatus and method of the present invention provide a number of advantages, including repeatability, since each exposure that is placed under AEC control can result in a known, fixed dose. This arrangement is less prone to errors that can result, for example, from variations in setup or from incorrect dosimeter positioning. In order to make the process more fully automated, a stored sequence of reference thresholds can be used for an imaging application. Once this is set up, no external instrumentation or equipment are required. Calibration can be automatically executed by an operator/technician upon entry of a suitable command instruction.

The invention has been described in detail with particular reference to certain preferred embodiments thereof, but it will be understood that variations and modifications can be effected within the scope of the invention as described above, and as noted in the appended claims, by a person of ordinary skill in the art without departing from the scope of the invention. For example, the method can be used with both DR systems and with other digital imaging sensors, such as CR cassettes and their associated reading equipment. The embodiments described in detail herein use the AEC sensor as the radiation sensor for digital X-ray detector calibration. However, it should be noted that an alternate type of sensor could be used, including a radiation sensor that is specifically disposed in position for X-ray detector calibration and removed once calibration exposures have been terminated. The method of the present invention can be used for systems that position the AEC sensor or other type of radiation sensor behind or in front of the detector.

Thus, what is provided is an apparatus and method for providing a predetermined exposure level for digital radiology (DR) detector calibration using an Automatic Exposure Control (AEC) device.

PARTS LIST

| | |
|---|---|
| 10. | X-ray apparatus |
| 12. | Patient |
| 14. | Table top |
| 16. | Emitter |
| 20. | Bucky |
| 22. | Grid |
| 24. | Detector |
| 26. | AEC sensor |
| 30. | Controller |
| 32. | Collimator |
| 36, 38, 40. | Curve |
| 42. | Line |
| 44. | Value |
| 46. | Register |
| 50. | Control loop |
| 52. | Gain control |
| 54. | Tables |
| 56. | Gain circuit |
| 64. | Calibration value |
| 66. | Calibration tables |
| 68. | Control logic processor |
| 70. | Comparator |
| S100. | Initialization step |
| S110. | Gain selection step |
| S120. | Beam conditions selection step |
| S130. | Load value step |
| S140. | Exposure step |
| S150. | Reading step |
| S160. | Correction values generation step |
| $D_A$, $D_B$, and $D_C$. | Digital value |
| $E_A$, $E_B$, and $E_C$. | Exposure value |
| O. | Optical path |

The invention claimed is:

1. A method for calibrating a digital X-ray detector, executed at least in part by a control logic processor, comprising:
   providing a radiation sensor along the optical path that extends between a radiation emitter and the digital X-ray detector;
   selecting a set of radiation beam conditions for X-ray generation;
   obtaining digital image values from the digital X-ray detector in one or more iterations of:
   (a) providing a threshold signal to radiation control logic, the threshold signal corresponding to a predetermined exposure level;
   (b) exposing both the digital X-ray detector and the radiation sensor to radiation, and terminating the exposure according to a comparison of the threshold signal with a signal from the radiation sensor that indicates an accumulated radiation level; and
   (c) obtaining the digital image values from the digital X-ray detector; and
   generating one or more sets of calibration values according to the obtained digital image values.

2. The method of claim 1 wherein selecting a set of radiation beam conditions comprises selecting one or more parameters from the group consisting of: a kVp value indicative of beam energy, an mA value indicative of beam intensity, an X-ray filter material, and a source-to-image distance between the radiation emitter and the digital X-ray detector.

3. The method of claim 2 wherein selecting a set of radiation beam conditions comprises prompting an operator for parameter entry.

4. The method of claim 1 wherein providing a threshold signal comprises providing a digital signal.

5. The method of claim 1 wherein providing a threshold signal comprises providing an analog signal.

6. The method of claim 1 further comprising:
   obtaining an image of a patient; and
   combining the one or more sets of generated calibration values with digital values obtained from the image of the patient.

7. The method of claim 1 wherein the step of exposing is initiated by an operator.

8. The method of claim 1 wherein the step of exposing is initiated automatically.

9. The method of claim 1 wherein two or more iterations use the same radiation beam conditions.

10. The method of claim 1 wherein two or more iterations use different radiation beam conditions.

11. The method of claim 1 wherein the radiation sensor is an automatic exposure control sensor.

12. The method of claim 11 further comprising conditioning an automatic exposure control gain signal for a predetermined range according to the digital X-ray detector.

13. The method of claim 12 wherein conditioning the automatic exposure control gain signal comprises making an adjustment to an automatic exposure control feedback signal.

14. The method of claim 1 wherein steps of selecting a set of radiation beam conditions, obtaining digital image values, and generating one or more sets of calibration values are executed as an automated calibration algorithm.

15. A method for calibrating a digital X-ray detector, executed at least in part by a control logic processor, comprising:

selecting a set of radiation beam conditions for X-ray generation;

obtaining digital image values from the digital X-ray detector in one or more iterations of:
 (i) providing a threshold signal to radiation control logic, the threshold signal corresponding to a predetermined exposure level;
 (ii) exposing both the digital X-ray detector and an automatic exposure control sensor to radiation, and terminating the exposure according to a comparison of the threshold signal with a signal from the automatic exposure control sensor that indicates an accumulated radiation level; and
 (iii) obtaining the digital image values from the digital X-ray detector; and generating one or more sets of calibration values according to the obtained digital image values.

16. The method of claim 15 wherein selecting a set of radiation beam conditions comprises selecting one or more parameters from the group consisting of a kVp value indicative of beam energy, an mA value indicative of beam intensity, an X-ray filter material, and a source-to-image distance between the radiation emitter and the digital X-ray detector.

17. The method of claim 15 wherein providing a threshold signal comprises providing a digital signal.

18. The method of claim 15 wherein providing a threshold signal comprises providing an analog signal.

19. The method of claim 15 further comprising:

obtaining an image of a patient; and combining the one or more sets of generated calibration values with digital values obtained from the image of the patient.

20. The method of claim 15 wherein the step of exposing is initiated by an operator.

\* \* \* \* \*